US012582312B2

(12) United States Patent　　　　　(10) Patent No.: US 12,582,312 B2
Dudee et al.　　　　　　　　　　　　(45) Date of Patent: Mar. 24, 2026

(54) SLIT LAMP AND BIOMICROSCOPE ASSEMBLY

(71) Applicants: Jitander Dudee, Lexington, KY (US); Aarnav Dudee, Lexington, KY (US)

(72) Inventors: Jitander Dudee, Lexington, KY (US); Aarnav Dudee, Lexington, KY (US)

( * ) Notice: Subject to any disclaimer, the term of this patent is extended or adjusted under 35 U.S.C. 154(b) by 384 days.

(21) Appl. No.: 18/200,768

(22) Filed: May 23, 2023

(65) Prior Publication Data

US 2023/0329550 A1　　Oct. 19, 2023

Related U.S. Application Data

(63) Continuation-in-part of application No. 17/062,689, filed on Oct. 5, 2020, now abandoned.

(60) Provisional application No. 62/910,018, filed on Oct. 3, 2019.

(51) Int. Cl.
　　*A61B 3/135*　　　　(2006.01)
　　*A61B 90/25*　　　　(2016.01)

(52) U.S. Cl.
　　CPC .............. *A61B 3/135* (2013.01); *A61B 90/25* (2016.02)

(58) Field of Classification Search
　　CPC ............................... A61B 3/135; A61B 3/0083
　　USPC .................................................. 351/214, 221
　　See application file for complete search history.

(56) References Cited

U.S. PATENT DOCUMENTS

| | | | | |
|---|---|---|---|---|
| 2,622,473 A | * | 12/1952 | Littmann | A61B 3/135 |
| | | | | 351/216 |
| 2,999,422 A | * | 9/1961 | Papritz | A61B 3/135 |
| | | | | 351/221 |

| | | | | |
|---|---|---|---|---|
| 4,411,502 A | * | 10/1983 | Lang | A61B 3/135 |
| | | | | 351/221 |
| 4,699,131 A | * | 10/1987 | Crook | A61F 9/007 |
| | | | | 128/206.28 |
| 4,874,236 A | * | 10/1989 | Abraham | A61B 3/135 |
| | | | | 351/205 |
| 5,094,521 A | * | 3/1992 | Jolson | A61B 3/11 |
| | | | | 351/210 |
| 6,283,596 B1 | * | 9/2001 | Yoshimura | A61B 3/135 |
| | | | | 351/214 |
| 6,474,815 B1 | * | 11/2002 | Ulbers | A61B 3/135 |
| | | | | 351/214 |
| 6,631,989 B2 | * | 10/2003 | Odom | A61B 3/145 |
| | | | | 351/205 |
| 7,118,218 B2 | * | 10/2006 | Barker | A61B 3/0083 |
| | | | | 351/200 |
| 7,819,528 B1 | * | 10/2010 | Dudee | A61B 3/0083 |
| | | | | 351/245 |

(Continued)

*Primary Examiner* — Zachary W Wilkes

(74) *Attorney, Agent, or Firm* — Black McCuskey

(57) ABSTRACT

A slit lamp and biomicroscope assembly can include a viewing system including a biomicroscope; an illumination system including a slit lamp with a light source and a light processing system with a first actuator; a positioning system supporting the biomicroscope and the slit lamp and including second and third actuators to position the biomicroscope along horizontal and vertical axes; and a user interface handle. The user interface handle can be graspable by a hand of a user and supported on the positioning system proximate to the biomicroscope such that a user looking into the biomicroscope can reach the user interface handle. The user interface handle can include a plurality of input devices including input devices in communication with the actuators.

7 Claims, 6 Drawing Sheets

(56)             References Cited

U.S. PATENT DOCUMENTS

| | | | |
|---|---|---|---|
| 7,922,329 B1* | 4/2011 | Graether | A61B 3/135 |
| | | | 351/205 |
| 2021/0100449 A1* | 4/2021 | Dudee | A61F 2/164 |

* cited by examiner

SLIT LAMP AND BIOMICROSCOPE ASSEMBLY

CROSS-REFERENCE TO RELATED APPLICATIONS

This application is a continuation-in-part of U.S. patent application Ser. No. 17/062,689, for IMPROVED SLIT LAMP AND BIOMICROSCOPE ASSEMBLY, filed 2020 Oct. 5, which claims the benefit of U.S. Prov. Pat. App. Ser. No. 62/910,018 for IMPROVEMENTS IN EYE CARE, filed on 2019 Oct. 3, both of which are hereby incorporated by reference in their entireties.

BACKGROUND

1. Field

The present disclosure corresponds generally to subject matter to optometry, such as eye examining and vision testing instruments, and more particularly relates to adjustable stands or bases which support ophthalmic diagnostic test instruments.

2. Description of Related Prior Art

U.S. Pat. No. 7,819,528 discloses a table-free mounting system for a slit lamp biomicroscope assembly. The apparatus provides a means for slit lamp biomicroscopes and similar opthalmological instruments to be accurately positioned and controlled without the need for a table base under the instrument, comprising an overhead assembly and mounting device which allows controlled movement and positioning of the slit lamp and associated illumination system in all three spatial axes. The overhead location of the support and movement mechanism combined with a joystick control on the instrument arm eliminates ergonomic obstacles allowing the instrument to be used when examining patients in wheelchairs and those affected by medical and anatomic restrictions.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A slit lamp and biomicroscope assembly can include a viewing system, an illumination system, a positioning system, and a user interface handle. The viewing system can include a biomicroscope. The illumination system can include a slit lamp having at least one light source and a light processing system. The light processing system can have at least one first actuator configured to control at least one attribute of a light beam light coming out of the slit lamp. The positioning system can support both of the biomicroscope and the slit lamp. The positioning system can include at least one second actuator configured to control a position of the biomicroscope along a first horizontal axis. The positioning system can also include at least one third actuator configured to control a position of the biomicroscope along a first vertical axis. The user interface handle can be graspable by a hand of a user and supported on the positioning system proximate to the biomicroscope such that a user looking into the biomicroscope can reach the user interface handle. The user interface handle can include a plurality of input devices including at least one first input device in communication with the at least one first actuator and at least one second input device in communication with the at least one second actuator and at least one third input device in communication with the at least third one actuator.

BRIEF DESCRIPTION OF THE DRAWINGS

The detailed description set forth below references the following drawings.

DETAILED DESCRIPTION

Figure 1:
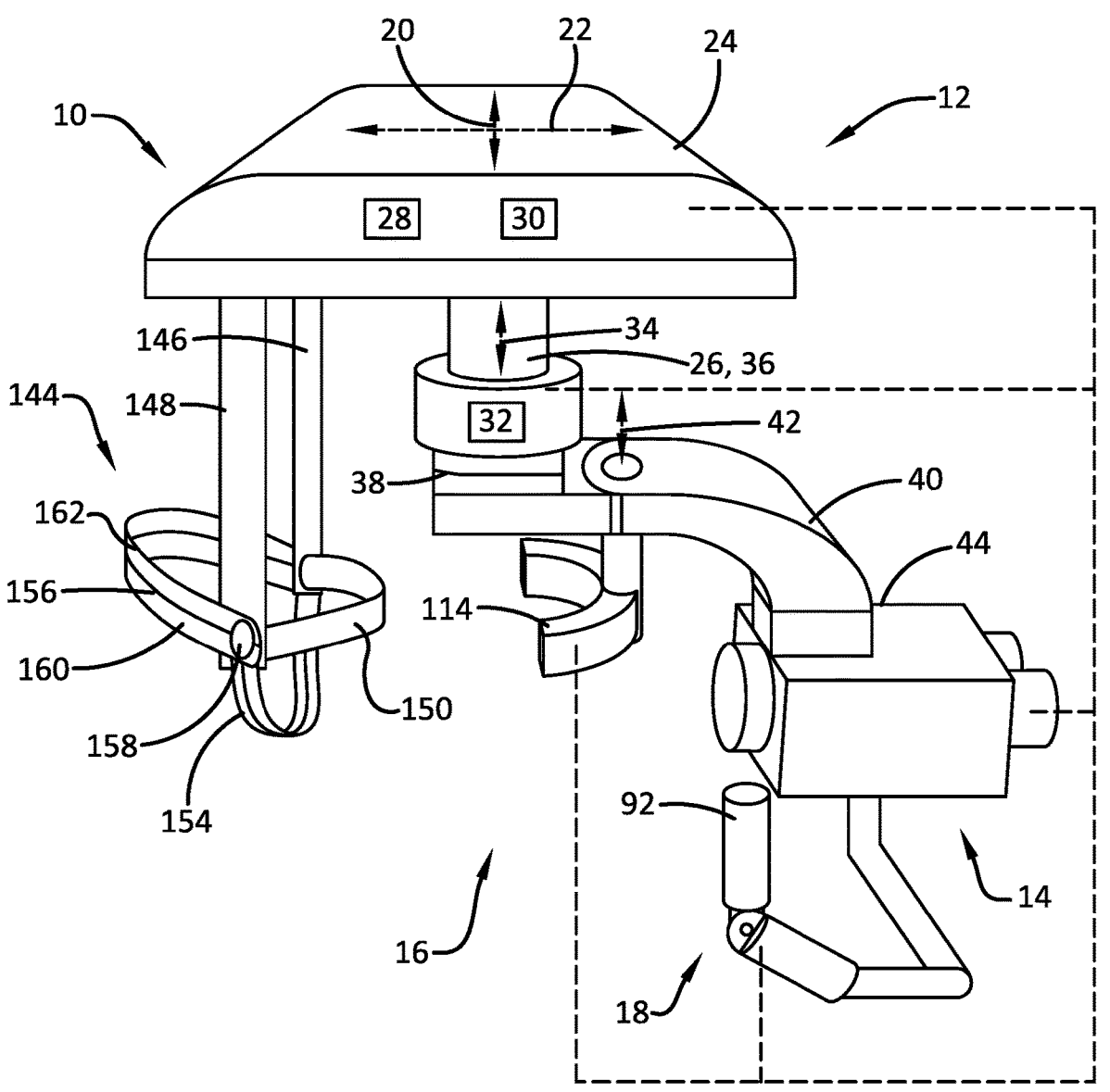
FIG. 1 is an isometric view of a slit lamp and biomicroscope assembly according to an exemplary embodiment of the present disclosure.

A plurality of different embodiments of the present disclosure is shown in the Figures of the application. Similar features are shown in the various embodiments of the present disclosure. Similar features across different embodiments have been numbered with a common reference numeral and have been differentiated by an alphabetic suffix. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The present disclosure, as demonstrated by the exemplary embodiments described below, provides an improved slit lamp and biomicroscope assembly. With reference now to FIG. 1, an exemplary slit lamp and biomicroscope assembly 10 can include a positioning system 12, a viewing system 14, an illumination system 16, and a user interface handle 18. The positioning system 12 can include at least one actuator configured to control a position of the biomicroscope along a first horizontal axis. The exemplary positioning system 12 includes a plurality of actuators configured to control a position of the biomicroscope along two horizontal axes. For illustrative purposes and not limitation, these horizontal axes are designated as X and Y axes, referenced at 20 and 22 in FIG. 1.

The exemplary positioning system 12 includes a base 24 and a telescoping shaft 26. An actuator 28 of the exemplary positioning system 12 is schematically shown in the base 24 and is configured to move the telescoping shaft 26 along the X axis 20. An actuator 30 of the exemplary positioning system 12 is schematically shown in the base 24 and is configured to move the telescoping shaft 26 along the Y axis 22. In one or more embodiments of the present disclosure, the base 24 can be a two-axis or multi-axis positioning system such as found at moticont.com/two-axis-positioning-systems.htm, www.ikont.com/technical-resources/technology-blog, or www.hiwin.com/linear-motors.html. The actuators 28, 30 can be an electrical, electro-mechanical, hydraulic, or pneumatic actuator operable to move a body, in this embodiment the shaft 26. In one example, an actuator applied in an embodiment of the present disclosure can include a worm screw driven in rotation by a motor and connected to a body such that rotation of the worm screw transmits rectilinear motion, such as motion of the shaft 26 relative to the base 24. The exemplary base 24 can include one or more tracks along which guide movement of an upper end of the shaft 26. In another example, an actuator applied in an embodiment of the present disclosure can include a telescoping cylinder extended or retracted by changing fluid pressure within the cylinder to transmit movement to the shaft 26. Other actuators could also be utilized, such as shown in the links above. The base 24 can be mounted on a ceiling. However, in other embodiments, the base 24 could be positioned on a floor or on a table.

The exemplary positioning system 12 also includes a third actuator 32 (schematically shown) configured to control extension and retraction of the telescoping shaft 26, to adjust a position of the viewing system 14 and the illumination system 16 along a vertical axis. The actuator 32 can be an actuator of any form described above. For illustrative purposes and not limitation, a vertical axis is designated as the Z axis, referenced at 34 in FIG. 1. The exemplary telescoping shaft 26 is bifurcated to allow an another aspect of adjusting movement. By way of example and not limitation, the exemplary telescoping shaft 26 includes mating telescoping shaft portions 36 and 38. The exemplary telescoping shaft 26 also includes a swing arm 40 connected to the telescoping shaft portion 38. The exemplary swing arm 40 can pivot relative to the exemplary telescoping shaft portion 38 about a pivot axis 42.

The exemplary viewing system 14 can include a biomicroscope 44. The exemplary positioning system 12 supports the exemplary biomicroscope 44. In the exemplary embodiment of the present disclosure, the biomicroscope 44 is fixed to an end of the swing arm 40. In one or more embodiments of the present disclosure, the exemplary biomicroscope 44 could be pivotally mounted to the swing arm 40 to add further degrees of freedom of movement.

Figure 3:
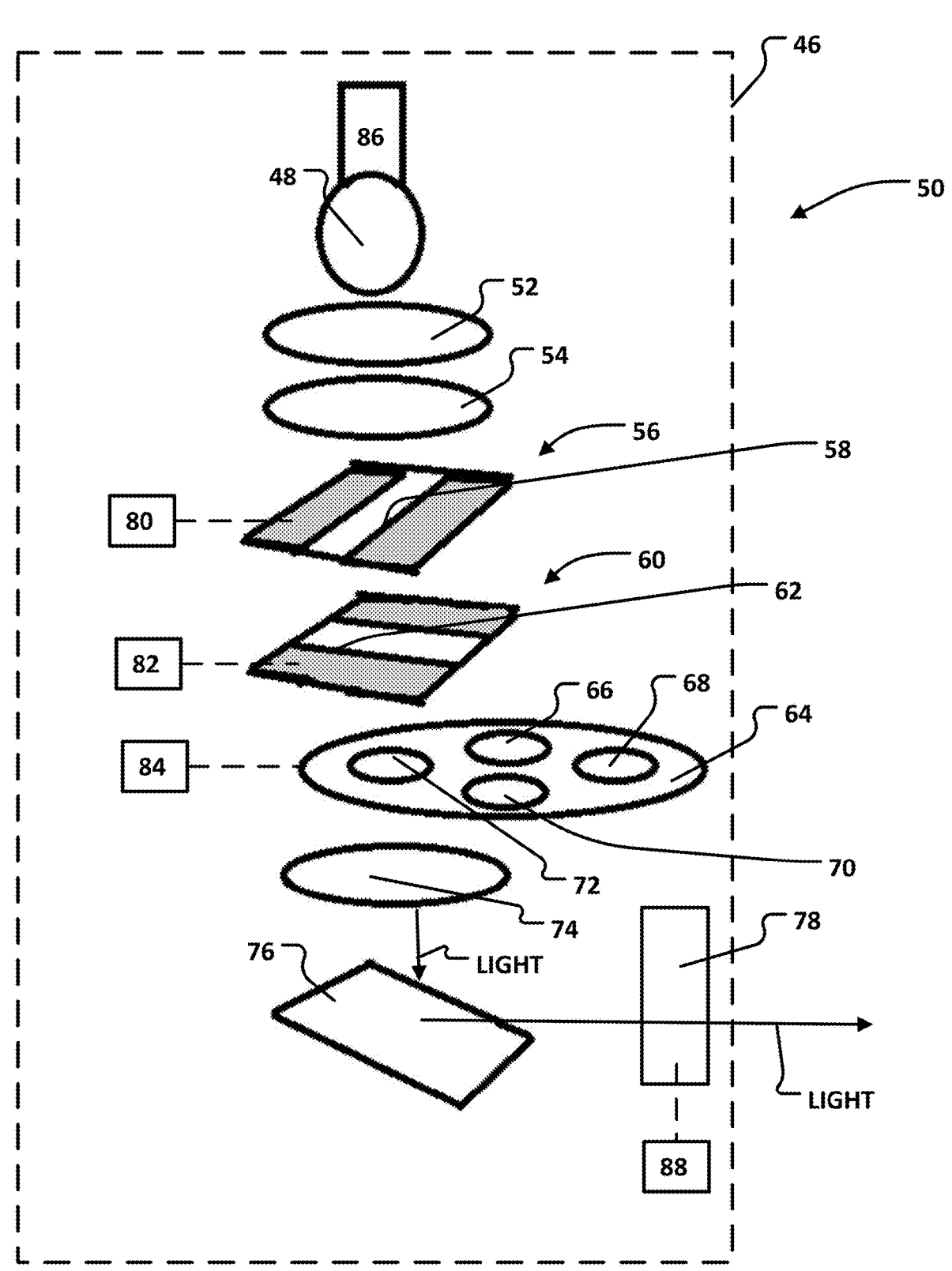
FIG. 3 is a schematic view of internal components of a slit lamp according to the exemplary embodiment of the present disclosure.

The exemplary illumination system 16 can include a slit lamp 46 having at least one light source 48 and a light processing system 50. FIG. 3 is a schematic view of the slit lamp 46. according to the exemplary embodiment of the present disclosure. The exemplary slit lamp 46 includes a light source 48 and a light processing system 50. The light source 48 can be any structure that emits light. The exemplary light processing system 50 includes condensers 52, 54; a first pane 56 defining a slit opening 58 of variable width; a second pane 60 defining a slit opening 62 of variable height; a rotatable carousel 64 supporting a plurality of filters 66, 68, 70, 72; a projection lens 74; a mirror 76; and an outlet 78. It is noted that the spatial arrangement of the components of the exemplary light processing system 50 can be selected as desired.

The exemplary positioning system 12 supports the slit lamp 46. Components of the slit lamp 46 can be positioned in the shaft portion 38. The light processing system 50 can have at least one actuator configured to control at least one attribute of a light beam light coming out of the slit lamp 46. Referring again to FIG. 3, the exemplary light processing system 50 includes an actuator 80 coupled to the pane 56 and configured to change a width of the slit opening 58 and thus change the attribute of the width of the light beam emitted by the slit lamp 46. The exemplary light processing system 50 also includes an actuator 82 coupled to the pane 60 and configured to change a height of the slit opening 62 and thus change the attribute of the height of the light beam emitted by the slit lamp 46. The exemplary light processing system 50 also includes an actuator 84 coupled to the carousel 64 and configured to rotate the carousel 64 and thus change the filter through which the light beam passes, which changes an attribute of the light beam. The actuators 80, 82, 84 can be an actuator of any form described above.

The exemplary light processing system 50 also includes a driver 86 coupled to the light source 48 configured to control either the voltage applied across the light source 48 or the current received by the light source 48, whereby the attribute of the brightness of the light beam is changed. The driver 86 can be an integrated circuit chip that can receive input from a user and, in response to such input, alter the voltage or current and thus change the light output of the light source 48. For example, input can be generated with a knob or a slide bar.

The exemplary light processing system 50 also includes an actuator 88 coupled to at least the outlet 78 and configured to at least move the outlet 78 to change the attribute of the direction of the light beam. In various embodiments of the present disclosure, the actuator 88 can be coupled to the entire slit lamp 46 or other components of the slit lamp 46 in addition to the outlet 78. The actuator 88 can be an actuator of any form described above.

Referring now also to FIG. 1, the exemplary user interface handle 18 is graspable by a hand of a user and supported on the positioning system 12 proximate to the exemplary biomicroscope 44 such that a user looking into the exemplary biomicroscope 44 can reach the exemplary user interface handle 18. The exemplary user interface handle 18 can include a plurality of input devices (detailed below) for communicating commands to the actuators 28-30 and 80-88. The user looking into the exemplary biomicroscope 44 can reach the input devices without looking at the input devices and while continuing to look through the exemplary biomicroscope 44 at the patient's eye. Further, the user can use one hand to engage the input devices while using the other hand for some other task carried out during the examination of a patient.

Figure 2:
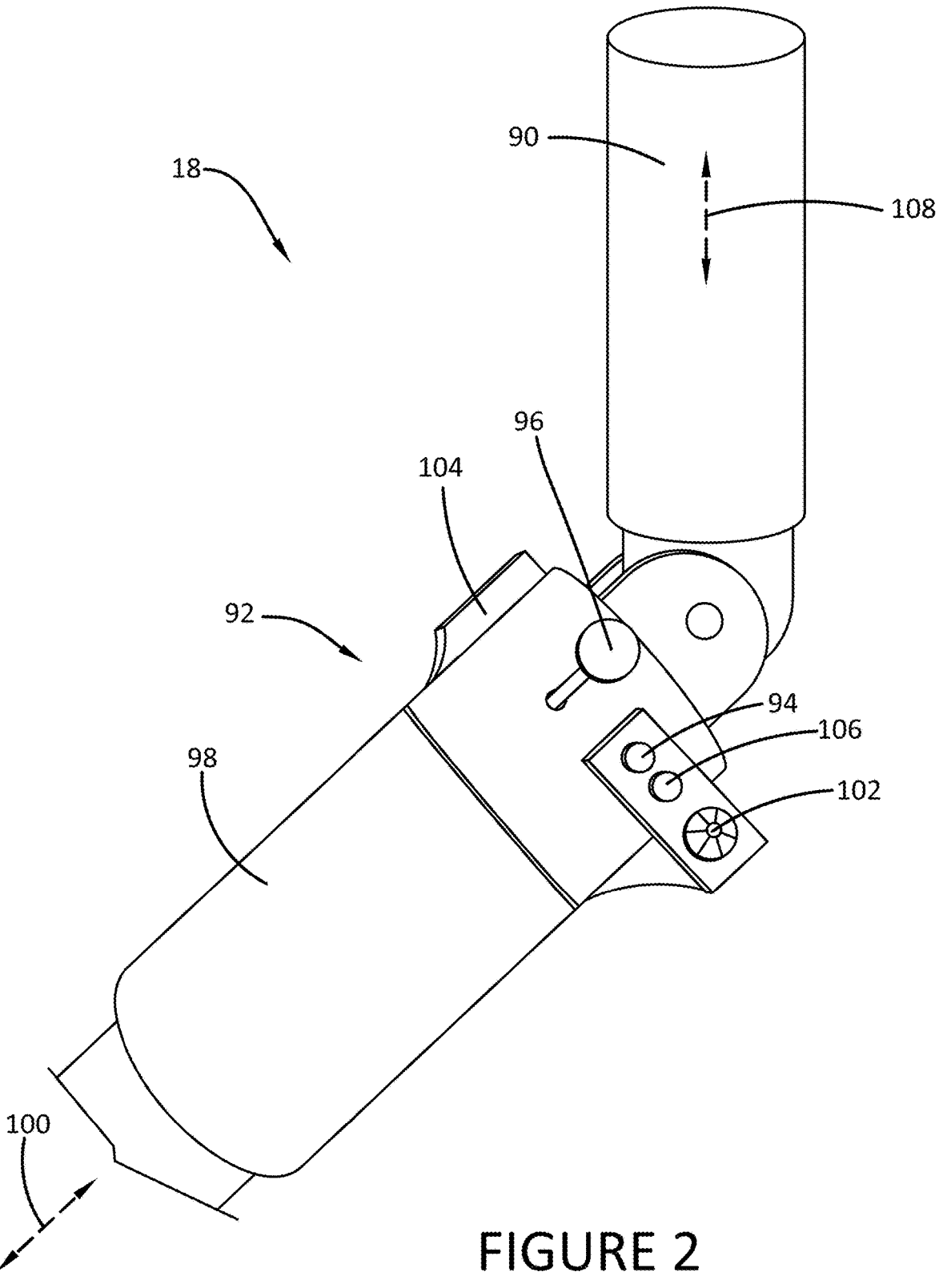
FIG. 2 is an isometric view user interface handle according to the exemplary embodiment of the present disclosure.

Referring now to FIGS. 1 and 2, the exemplary user interface handle 18 includes a first gripping portion 90 and a second gripping portion 92. The exemplary first gripping portion 90 and the exemplary second gripping portion 92 are mounted to the exemplary viewing system 14 and thus supported indirectly by the positioning system 12. The exemplary first gripping portion 90 and the exemplary second gripping portion 92 are adjacent to one another. The exemplary first gripping portion 90 is sized to be grasped by the hand of the user and configured to be grasped for gross movement of the exemplary biomicroscope 44 to a desired general position. The input devices are mounted on the exemplary second gripping portion 92.

The exemplary first gripping portion 90 is a simple handle, a solid cylindrical structure. The first gripping portion 90 can be other shapes in other embodiments, such as a spherical ball or some other shape. The first gripping portion 90 can be sufficiently sturdy and robust, as the first gripping portion 90 is grasped by the user when establishing a gross position for the viewing system 14 and the illumination system 16.

It is noted that the positioning system 12 can also include one or more counter-balances that maintain the exemplary biomicroscope 44 in the desired general position when the position is selected by the user after the user disengages the exemplary first gripping portion 90. A magnifying lens lamp has such counter-balances in the form of springs, which can also be applied in the exemplary positioning system 12. The various actuators 28-30 for controlling portions of the positioning system 12 can be configured to not inhibit adjusting movement of the portions of the positioning system 12 by hand.

The positioning system 12 can also include locks associated with each of the various actuators 28-30 that are configured to engage and prevent movement in response to signals received from one of the input devices. For example, a user can use the exemplary first gripping portion 90 to position the biomicroscope 44 close to the final, desired position. The user can then release the exemplary first gripping portion 90 and engage one of the input devices to move the biomicroscope in small, precise increments. When the user engages one of the input devices, the signal generated by that input device can be received by the actuators 28-30 or a master controller of the actuators 28-30 and, in response to the signal activate locks so that movement of the biomicroscope 44 is only permitted in response to further signals from the input devices. It is noted that dash lines in FIG. 1 represent pathways of electronic communication.

Referring now to FIG. 2, the second gripping portion 92 is sized to be grasped by the hand of the user. The exemplary plurality of input devices include a first input device in the form of a push button 94. The exemplary push button 94 is in communication with at least one of the actuators 80-88. In one embodiment, the exemplary push button 94 is in communication with the actuator 80 and, in response to the user pressing the push button 94, the width of the slit opening 58 increases or decreases. In another embodiment, the exemplary push button 94 is in communication with the actuator 82 and, in response to the user pressing the push button 94, the height of the slit opening 62 increases or decreases. In another embodiment, the exemplary push button 94 is in communication with the actuator 84 and, in response to the user pressing the push button 94, the carousel 64 rotates ninety degrees and positions a different filter in the pathway of the light beam. In another embodiment, the exemplary push button 94 is in communication with the driver 86 and, in response to the user pressing the push button 94, the driver 86 can alter the current delivered to the light source 48 such that light emission begins or ceases. In another embodiment, the exemplary push button 94 is in communication with the actuator 88 and, in response to the user pressing the push button 94, the at least the outlet 88 of the slit lamp 46 moves rectilinearly and/or rotationally. The description above is provided to demonstrate that any of the forms of input device can be placed in communication with any of the various actuators.

It is noted that one or more embodiments of the present disclosure can include speakers and database of audio files so that changes that can be seen and/or validated by the user, when the user is looking through the biomicroscope 44, can be communicated audibly. For example, if the carousel 64 is rotated, an audio file can be retrieved from a database by a controller and played through a speaker, wherein the audio file advises the user what filter is now in the pathway of the light beam. It is noted that the exemplary embodiment also includes input devices in the form of buttons 104 and 106.

The exemplary plurality of input devices include a second input device in the form of a joystick 96. In one embodiment, the exemplary joystick 96 is in communication with the actuator 28 and, in response to the user laterally pressing the joystick 96 in a first direction, the telescoping shaft 26 can move along the X axis 20. Further, in the embodiment, the exemplary joystick 96 is also in communication with the actuator 30 and, in response to the user laterally pressing the joystick 96 in a second direction perpendicular or orthogonal to the first direction, the telescoping shaft 26 can move along the Y axis 22. The exemplary joystick 96 can thus communicate with two actuators. In other embodiments of the present disclosure, the exemplary joystick 96 could communicate with one or more of the actuators 80-88.

The exemplary plurality of input devices include a third input device in the form of a rotatable sleeve 98. In one embodiment, the exemplary rotatable sleeve 98 is in communication with the actuator 32 and, in response to the user rotating the rotatable sleeve 98 about an axis 100 in a first rotational direction, the telescoping shaft 26 can extend, causing the viewing system 14 and illumination system 16 to lower. In response to the user rotating the rotatable sleeve 98 about the axis 100 in a second rotational direction opposite to the first rotational direction, the telescoping shaft 26 can retract, causing the viewing system 14 and illumination system 16 to raise. In other embodiments of the present disclosure, the exemplary rotatable sleeve 98 could communicate with one or more of the actuators 80-88.

The exemplary plurality of input devices include a fourth input device in the form of a rotatable knob 102. In one embodiment, the exemplary rotatable knob 102 could be in communication with the actuator 32 to control the telescoping shaft 26 instead of the rotatable sleeve 98. One or more rotatable knobs could be utilized to communicate with the actuators 80 and 82 to control the sizes of the slit openings 58, 62. A rotatable knob could be utilized to communicate with the actuators 28 and 30 to control the movement of the telescoping shaft 26 along the axes 20, 22. A rotatable knob could be utilized to communicate input signals to the driver 86 which result in a change in the brightness of the light source 48. A rotatable knob could be utilized to communicate a signal to the actuator 88 to move the outlet 78.

It is noted that other forms of input devices are contemplated by the present disclosure. By way of example and not limitation, slide bars and triggers could be utilized in other embodiments.

The exemplary input devices 94, 96, 98, 102, 104, 106 are mounted on the exemplary second gripping portion 92 and thus spaced from the exemplary first gripping portion 90.

The exemplary first gripping portion 90 is centered on a first longitudinal axis 108. The exemplary second gripping portion 92 is centered the axis 100. The exemplary first longitudinal axis 108 and the exemplary second longitudinal axis 100 are transverse to on another. This arrangement creates a distinction in the tactile feel of the exemplary first gripping portion 90 and the exemplary second gripping portion 92 so that the user can continue to look through the exemplary biomicroscope 44 while moving his/her hand along the exemplary user interface handle 18 from the gross movement handle to the fine movement controls provided by the input devices 94, 96, 98, 102, 104, 106.

As best shown in FIG. 1, the exemplary first gripping portion 90 is positioned above the exemplary second gripping portion 92. This position is another benefit in making it easier for a user, not looking at the user interface handle 18, to move his/her hand between the exemplary first gripping portion 90 and the exemplary second gripping portion 92 without looking at them. Further, the portion of the user interface handle 18 bearing the input devices is lower and user can rest his/her arm while controlling the actuators.

The exemplary first gripping portion 90 and the exemplary second gripping portion 92 are adjustably engaged with one another. The angle between the first longitudinal axis 108 and the axis 100 is selectable. FIG. 2 shows a yoke connection between the exemplary first gripping portion 90 and the exemplary second gripping portion 92 that can be loosened to change the angle and tightened when the desired angle is defined. This feature allows users to customize the positions of the exemplary first gripping portion 90 and the exemplary second gripping portion 92 relative to one another to enhance the user's comfort and inhibit distraction from occurring.

Figure 6:
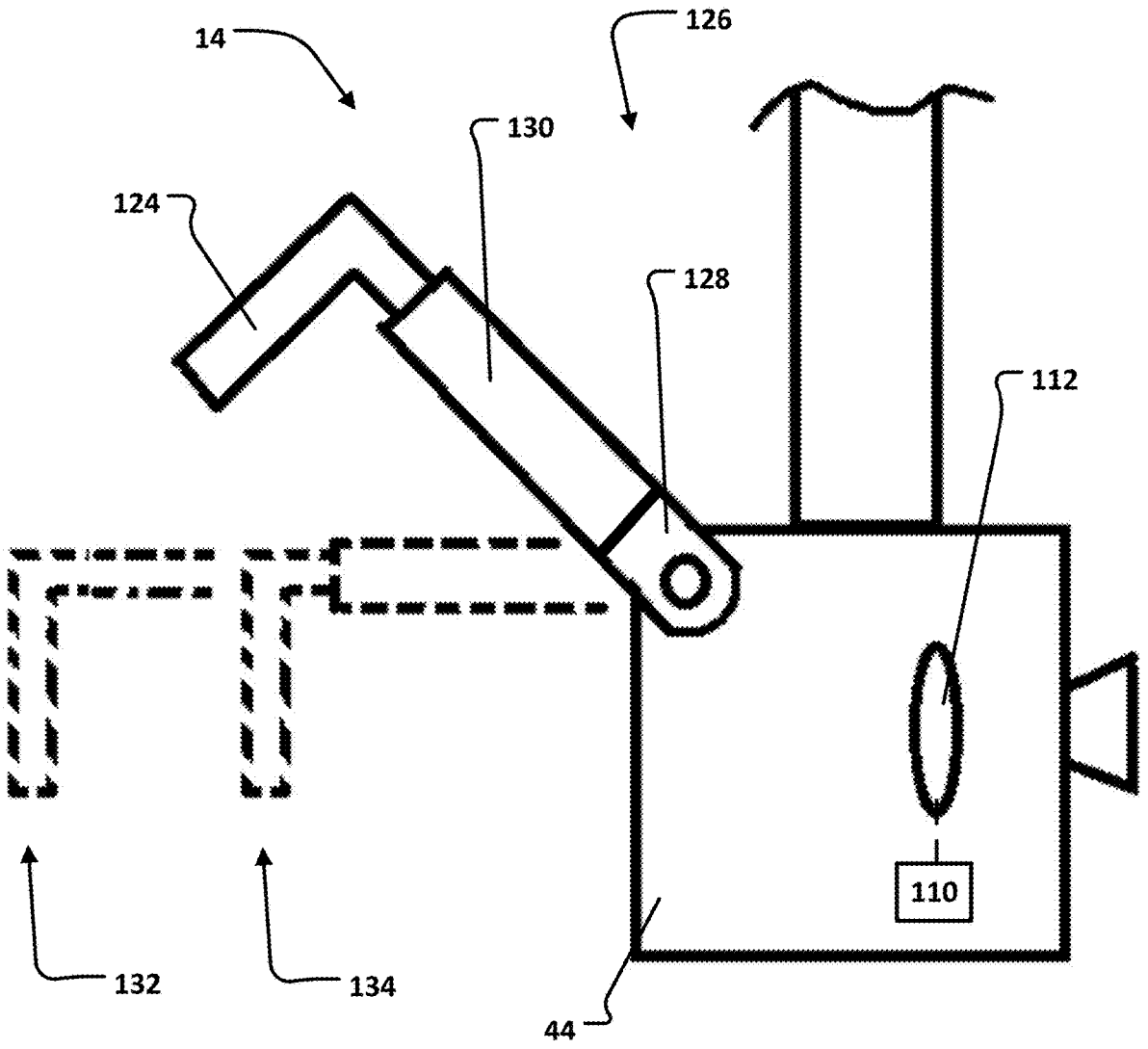
FIG. 6 is a partial side view of the slit lamp and biomicroscope assembly according to the exemplary embodiment of the present disclosure.

Referring now to FIG. 6, in one or more embodiments of the present disclosure, the exemplary biomicroscope 44 further comprises at least one lens 112 and an actuator 110 configured to move the lens 112 within the exemplary biomicroscope 44. The plurality of input devices on the second gripping portion 92 can include an input device in communication with the actuator 110. This feature is beneficial as it incorporate more control of the assembly 10 in the second gripping portion 92.

Figure 4:
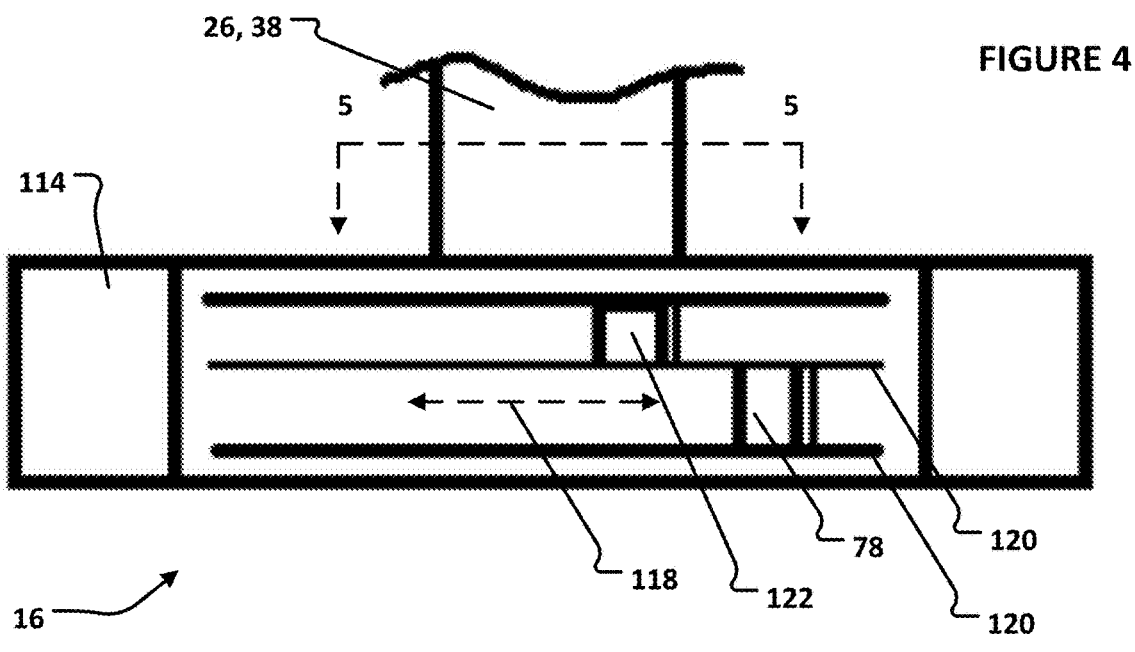
FIG. 4 is a front view of a portion of the slit lamp and biomicroscope assembly according to the exemplary embodiment of the present disclosure.
Figure 5:
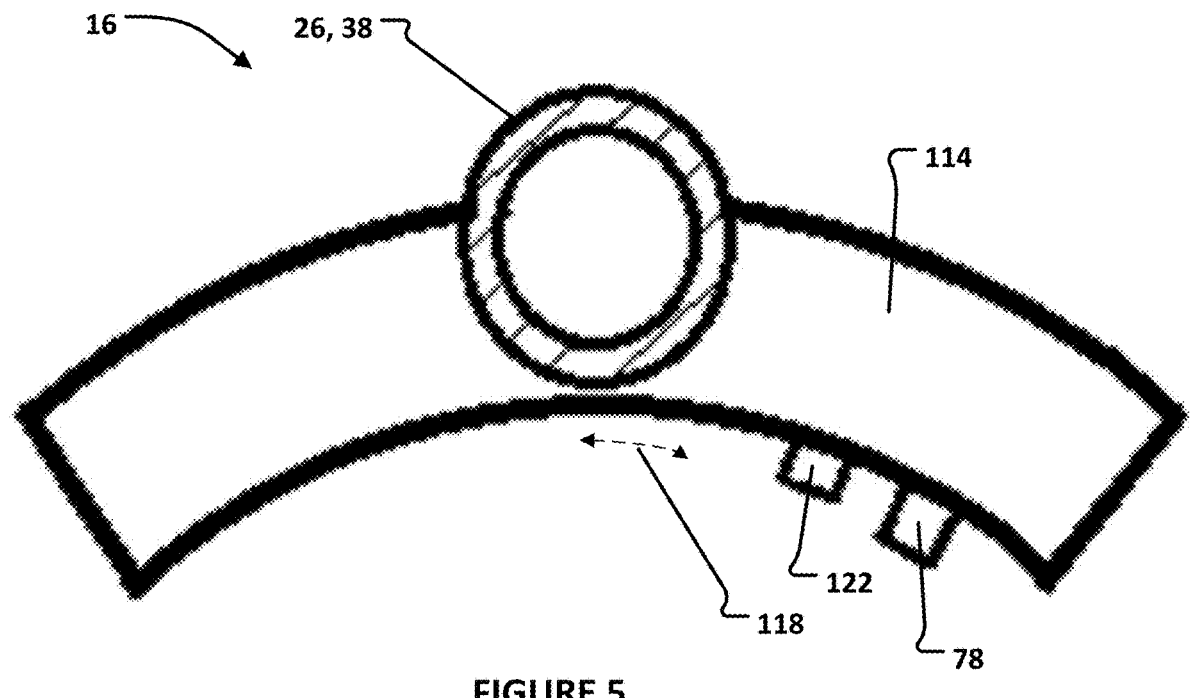
FIG. 5 is a partial cross-section taken through section lines 5-5 in FIG. 4.

Referring now to FIGS. 4 and 5, the exemplary illumination system 16 further comprises a frame 114. The exemplary frame 114 is supported by the positioning system 12 and has an arcuate surface 116 facing toward the patient. All or part of the exemplary slit lamp 46 can be positioned in the frame 114. The outlet 78 can be positioned on the arcuate surface 116 and thus directed at the patient. The actuator 88 can be positioned in or on the frame 114 can be configured to move the outlet 78 about the surface 116. Movement of the outlet 78 is referenced by arrow 118. Lines referenced at 120 represent tracks in the surface 116 that guide movement of the outlet 78. The exemplary slit lamp 46 is thus configured to emit light from a plurality of different locations along the arcuate surface 116. In alternative embodiment of the present disclosure, a slit lamp 46 could include multiple outlets at various fixed locations about the surface 116 to emit light from a plurality of different locations along the arcuate surface 116. The use of multiple light sources can allow multiple self-imposed light beams useful in measurement photography and for guiding patient fixation and eye movements and also for utilizing pupillary reactions and performing additional tests.

The exemplary assembly can also include a secondary light source 122 mounted to the arcuate frame 114. The secondary light source 122 can be utilized as a fixation source, wherein the patient is directed to focus on the secondary light source 122. The exemplary light source 122 can be moveable along the arcuate surface 116 like the outlet 78. Alternatively, the light source 122 can be defined by an array of light emitting diodes arranged around the arcuate profile of the frame 114.

Referring now to FIG. 6, the exemplary assembly 10 can also include a secondary lens 124 and a frame 126. The secondary lens 124 can augment the magnifying power of lenses in the biomicroscope 44. The frame 126 can support the secondary lens 124 and can be mounted to the exemplary biomicroscope 44. The exemplary frame 126 is moveable relative to the exemplary biomicroscope 44 between first second end limits of travel. When the frame 126 is at the first end limit of travel as shown in solid line, the secondary lens 124 is positioned in the field of view of the exemplary biomicroscope 44. When the frame 126 is at the second end limit of travel the secondary lens 124 is positioned outside of the field of view of the exemplary biomicroscope 44.

The exemplary frame 126 includes a bracket portion 128 pivotally mounted to the exemplary biomicroscope 44. The exemplary frame 126 also includes at least one telescoping arm assembly 130 positioned between the bracket portion 128 and the secondary lens 124. When the at least one telescoping arm assembly 130 is in an extended configuration, the secondary lens 124 is positioned a first distance from the exemplary biomicroscope 44 (referenced at 132). When the at least one telescoping arm assembly 130 is in a retracted configuration, the secondary lens 124 is positioned a second distance from the exemplary biomicroscope 44 (referenced at 134), less than the first distance. This allows the position of the secondary lens 124 to be adjustable.

The secondary lens 124 enhances visualization of structures of the eye. Such lens being placed within the line of the site of the examiner or retracted, as desired depending on its use. The fine positioning of the lens 124 can be controlled by one of the input devices on the second gripping portion 92. The frame 126 can be flexible, but constructed so that it will not alter its shapes simply from the weight of the lens so that once the lens is adjusted may be left in place allowing the hand free for use in performing other procedures or manipulation as required. The frame 126 may also incorporate a spring so that its support can move in the anterior posterior axis preventing the lens from abutting on the patient's face should the biomicroscope be moved forward excessively. It is noted that the secondary lens 124 and frame 126 is not shown in FIG. 1 in order to enhance the clarity of other structures in FIG. 1.

Figures 7, 8:
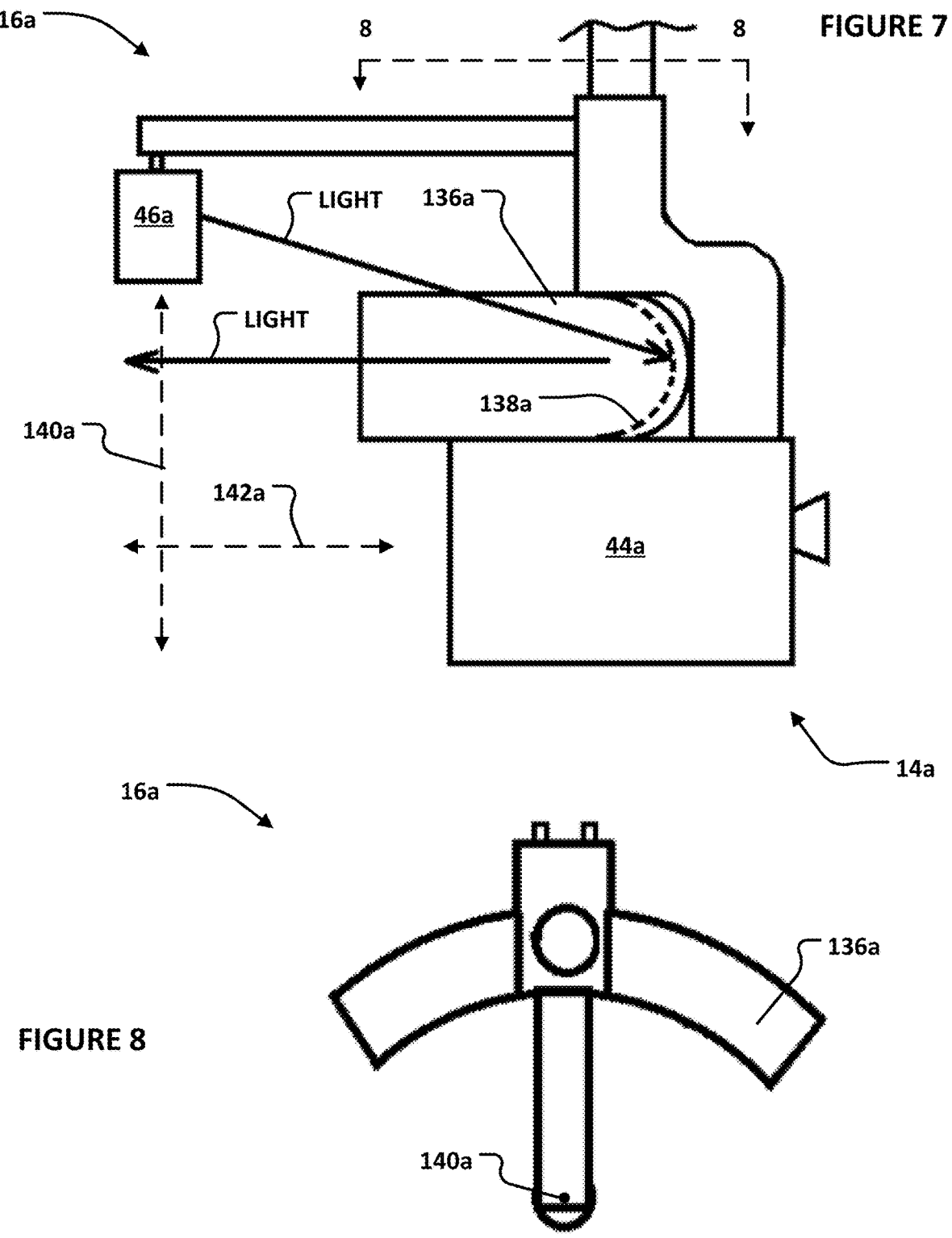
FIG. 7 a partial side view of a slit lamp and biomicroscope assembly according to another exemplary embodiment of the present disclosure.
FIG. 8 is a partial cross-section taken through section lines 8-8 in FIG. 7.

Referring now to FIGS. 7 and 8, in another embodiment of the present disclosure, a slit lamp and biomicroscope assembly 10 can include an illumination system 16a that includes a mirror 136a defining an arcuate reflecting surface 138a. In FIG. 7, the arcuate reflecting surface 138a is shown in dash line since it is hidden (FIG. 7 is not a cross-section). The exemplary arcuate reflecting surface 138a is centered on and extends about a mirror axis 140a perpendicular to an optic axis 142a of the exemplary biomicroscope 44a. It is noted that the profile of the arcuate reflecting surface 138a is the same about axis 140a. An exemplary slit lamp 46a of the illumination system 16a is as mounted at the mirror axis 140a whereby the mirror axis 140a extends through the slit lamp 46a. The exemplary slit lamp 46a is rotatable about the mirror axis 140a, and thus reflects light off of different portions of the surface 138a. The surface 138a is shaped and the slit lamp 46a is positioned such that light is always directed toward the patient, but from different directions. It is noted that the arrows in solid line represent the light beam. The use of an aspheric mirror allows full angle of instant beams with less lateral width, thereby, reducing obstruction. Furthermore, the mirror rather than being a continuous band can be separated and consist of a few elements chosen to provide the most commonly utilized illumination angles, in ones which can be quickly varied for the left and right eye.

Referring again to FIG. 1, the exemplary assembly 10 also includes a head support system 144. The exemplary head support system 144 includes first and second vertical bars 146, 148 extending from the positioning system 12. The exemplary head support system 144 also includes a forehead support 150 extending between the first and second vertical bars 146, 148. The exemplary head support system 144 also includes a chin strap/rest 154 extending between the first and second vertical bars 146, 148. The exemplary head support system 144 also includes a back strap 156 connected to the chin rest 154 and configured to extend around a back of a patient's head. The forehead support 150, the chin strap 154, and the back strap 156 can be interconnect at their respective ends by a pulley or rivet, such as pulley 158. The chin strap 154 and the back strap 156 can each be formed with adjacent segments having different elasticities. For example, the back strap 156 can be formed from segments 160, 162 stitched together along their sides. The segments 160, 162 can have different elasticities, wherein segment 160 generates a larger force when stretched than the segment 162. The head support system 144 assists in stable head positioning of patient and links to vertical position of the examining instrument to minimize the need for adjustment. In operation, the strap 156 can be held upwardly and the strap can be held to the right (based on the perspective of FIG. 1). The patient can then rest his/her forehead against the forehead support 150. Next, the strap 156 can be drawn over the back of the patient's head and the strap 154 can be pulled around the patient's chin and jaw.

One or more embodiments of the present disclosure can include an integrated video display system. Such a system could present video to the user while the user is looking into the biomicroscope 44. Such a system would be useful, as the user could be presented with recordings of previous examinations of the same patient for efficient and accurate comparison.

One or more embodiments of the present disclosure can include light sources configured to cooperatively generate multiple polarized light beams, of variable intensity and direction of polarization. A dual slit lamp illumination beam can be comprised of polarized light filtered orthogonally, a relative proportion of each direction of polarized illumination can be varied to improve visualization of ocular structures.

One or more embodiments of the present disclosure can include infra-red viewing and photography, to reduce the need for dilation and to assist in measuring pupil size. Such an illumination system can use infrared light projected onto the eye in dim conditions to minimize pupillary constriction in response to visible light, thereby allowing examination of the posterior structures of the eye behind the iris with reduced need for mydriatic eyedrops to dilate the pupils. Biomicroscope with infrared cameras can project images on eyepiece screens viewable through the oculars by the examiner and can provide a stereoscopic view of the eye through scotopic pupils (dilated in response to low illumination).

One or more embodiments of the present disclosure can include a system for mapping three-dimensional locations of reference points, visualized in combination with pinpoint aiming beams. In such a system, a pair of laser aiming beams can be focused at an observers point of fixation at high magnification so that the depth of focus is minimal. A means of recording the three-dimensional coordinates of the point of fixation is achieved using a computer. The point of fixation can then be moved to another part of the ocular structure and subsequent three-dimensional coordinates can be recorded. In this manner and accurate measurement of ocular dimensions can be achieved and their dynamic variation recorded. Such dimensions include the minimum and maximum anterior chamber depths, movement of intraocular lenses, corneal thickness, morphology of lesions and the flow of convection currents within the eye.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or subcombinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:

1. A slit lamp and biomicroscope assembly comprising:
a viewing system including a biomicroscope;
an illumination system including a slit lamp having at least one light source and a light processing system having a first pane having a first slit opening of variable width and a second pane having a second slit opening of variable height and a carousel configured to rotate and an outlet configured to move;
a positioning system supporting both of said biomicroscope and said slit lamp, said positioning system configured to control a position of said biomicroscope along a first horizontal axis and along a first vertical axis; and
a user interface handle graspable by a hand of a user and supported on said positioning system proximate to said biomicroscope, said user interface handle including a plurality of input devices including at least one first input device and at least one second input device and at least one third input device;
wherein said user interface handle further comprises a first gripping portion and a second gripping portion adjacent to one another;
wherein said first gripping portion is sized to be grasped by the hand of the user and configured to be grasped for gross movement of said biomicroscope to a desired general position;
wherein said second gripping portion is also sized to be grasped by the hand of the user;
wherein said at least one second input device is mounted on said second gripping portion and thus spaced from said first gripping portion, said at least one second input device configured to receive input from the hand of the user; and
wherein said at least one third input device is mounted on said second gripping portion and thus spaced from said first gripping portion, said at least one third input device configured to receive input from the hand of the user.

2. The slit lamp and biomicroscope assembly of claim 1 wherein said first gripping portion is centered on a first longitudinal axis, said second gripping portion is centered on a second longitudinal axis, and said first longitudinal axis and said second longitudinal axis are transverse to one another.

3. The slit lamp and biomicroscope assembly of claim 1 wherein said first gripping portion is positioned above said second gripping portion.

4. The slit lamp and biomicroscope assembly of claim 1 wherein said first gripping portion is centered on a first longitudinal axis, said second gripping portion is centered on a second longitudinal axis, and said first gripping portion and said second gripping portion are adjustably engaged with one another whereby an angle between said first longitudinal axis and said second longitudinal axis is selectable.

5. The slit lamp and biomicroscope assembly of claim 1 wherein said plurality of input devices includes at least two of a group consisting of a push button, a joystick, a rotatable sleeve, and a rotatable knob.

6. The slit lamp and biomicroscope assembly of claim 1 wherein both of said first gripping portion and said second gripping portion are further defined as mounted to said viewing system and thus supported indirectly by said positioning system.

7. The slit lamp and biomicroscope assembly of claim 1 wherein:
  said at least one first input device is mounted on said second gripping portion and thus spaced from said first gripping portion; and
  said at least one first input device is configured to receive input from the hand of the user.

\* \* \* \* \*